United States Patent

Hart et al.

[11] Patent Number: 5,803,919
[45] Date of Patent: Sep. 8, 1998

[54] TROCAR VALVE ASSEMBLY

[75] Inventors: Charles C. Hart, Huntington Beach; Henry Kahle, Irvine, both of Calif.

[73] Assignee: Applied Medical Resources Corporation, Laguna Hills, Calif.

[21] Appl. No.: 363,734

[22] Filed: Dec. 23, 1994

Related U.S. Application Data

[63] Continuation-in-part of Ser. No. 51,609, Apr. 23, 1993, Pat. No. 5,443,452, which is a continuation of Ser. No. 907,706, Jul. 2, 1992, abandoned.

[51] Int. Cl.$^6$ .................................................. A61M 5/178
[52] U.S. Cl. ........................................... 604/167; 604/256
[58] Field of Search ................................... 604/167, 296, 604/247, 256; 137/846, 849

[56] References Cited

U.S. PATENT DOCUMENTS

| | | |
|---|---|---|
| 3,861,416 | 1/1975 | Wichterle . |
| 4,143,853 | 3/1979 | Abramson . |
| 4,177,814 | 12/1979 | Knepshield et al. . |
| 4,222,126 | 9/1980 | Boretos et al. . |
| 4,364,127 | 12/1982 | Pierce et al. . |
| 4,375,864 | 3/1983 | Savage . |
| 4,424,833 | 1/1984 | Spector et al. . |
| 4,475,548 | 10/1984 | Muto . |
| 4,492,253 | 1/1985 | Raftis . |
| 4,535,819 | 8/1985 | Atkinson et al. . |
| 4,566,493 | 1/1986 | Edwards et al. . |
| 4,673,393 | 6/1987 | Suzuki et al. . |
| 4,765,588 | 8/1988 | Atkinson . |
| 4,798,584 | 1/1989 | Hillsted . |
| 4,809,679 | 3/1989 | Shimonaka et al. . |
| 5,010,925 | 4/1991 | Atkinson et al. . |
| 5,141,498 | 8/1992 | Christian . |

*Primary Examiner*—Sam Rimell
*Attorney, Agent, or Firm*—Richard L. Myers

[57] ABSTRACT

A surgical device having a longitudinal configuration and an axis extending between a proximal end and an opposing distal end includes a housing having an inner surface defining a chamber and a cannula extending distally of the housing. A valve disposed in the housing has a conical outer wall and a plurality of distal walls which form a first seal with the inner surface of the housing and a second seal. The walls include multiple fold segments which are foldable between a first position wherein the second seal closes the cannula and a second position wherein the second seal opens the cannula. A method for actuating the valve includes the step of inserting an instrument distally into the valve to contact the fold segments along a line and to move the fold segments to the second position.

17 Claims, 5 Drawing Sheets

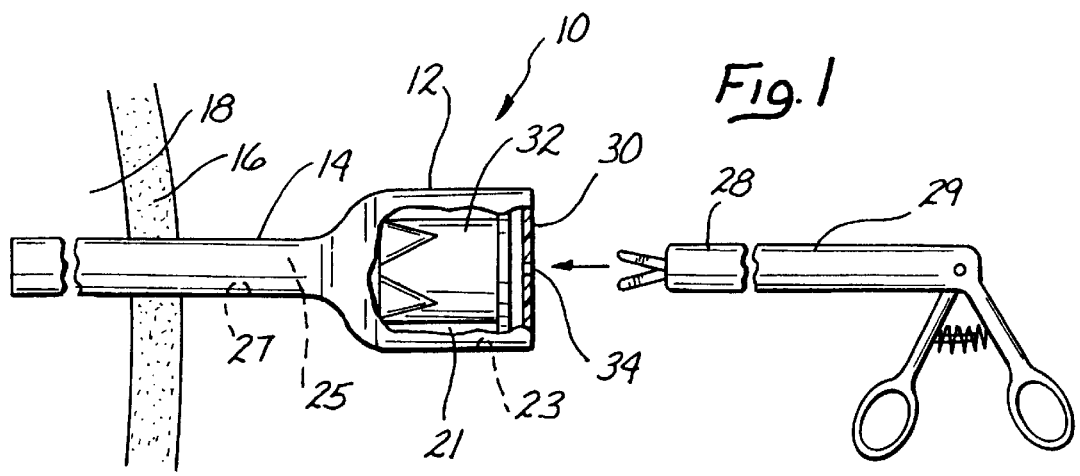
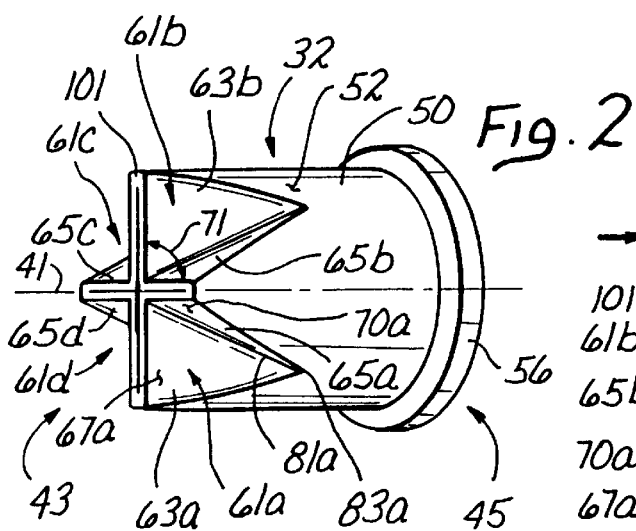
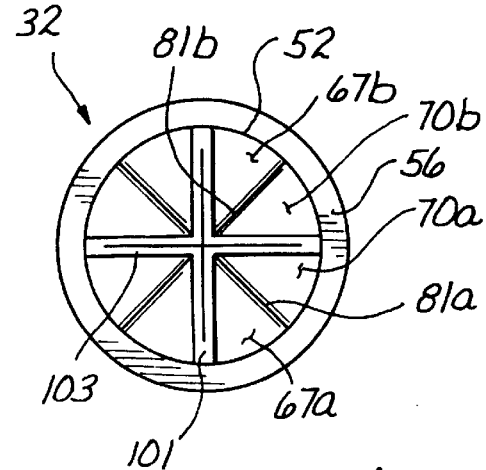
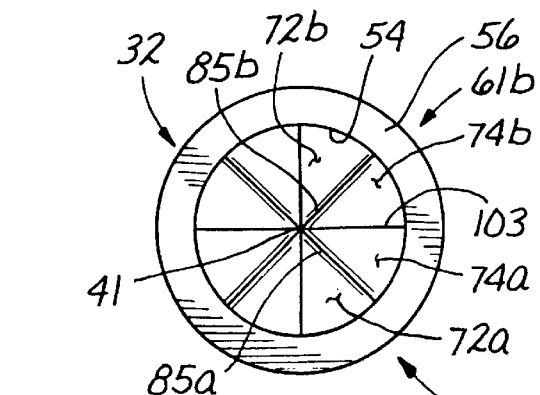
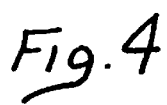

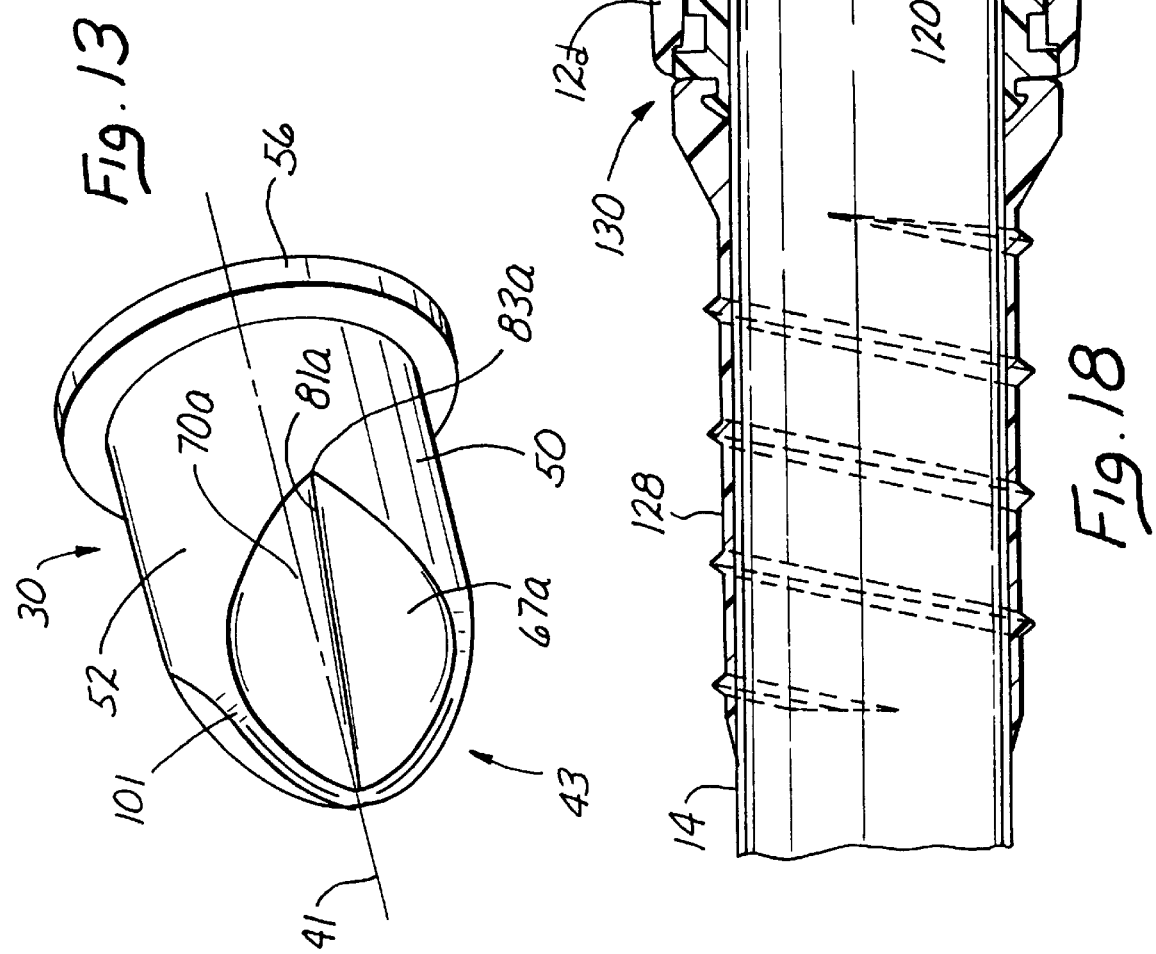

5,803,919

TROCAR VALVE ASSEMBLY

CROSS REFERENCE

This application is a continuation-in-part of U.S. patent application Ser. No. 08/051,609 filed on Apr. 23, 1993, now U.S. Pat. No. 5,443,452 which is a continuation of U.S. patent application Ser. No. 07/907,706 filed on Jul. 2, 1992, now abandoned.

BACKGROUND OF THE INVENTION

1. Field of the Invention

This invention relates generally to access devices and more specifically to seals and other closure mechanisms applicable to such devices.

2. Discussion of the Prior Art

Access devices are commonly used in surgery to facilitate the introduction of various surgical instruments into vessels, conduits, cavities, and other interior regions of the body. These access devices include, for example, devices which facilitate introduction of a needle into a vessel, and trocars which facilitate the introduction of laparoscopic instruments into the abdomen of the body.

Some of these access devices are introduced into regions which include a fluid under pressure. In the case of a needle access device, this fluid may be a liquid such as blood. In the case of a trocar, this fluid may be a gas such as an insufflation gas. In either case it is desirable to provide for the introduction of the surgical instrument into the cavity without permitting the escape of the pressurized fluid.

Seal mechanisms are usually employed in an access device to prevent this escape of fluid. Such mechanisms have typically included an aperture or septum valve which has functioned satisfactorily to form a seal around the outer surface of an instrument positioned within the access device. However, when this instrument has been removed, such aperture or septum valves have been relatively ineffective in providing a complete closure or zero closure to prevent the escape of pressurized fluid. For this reason, a zero closure valve has typically been included in the seal mechanism. While zero closure valves are typically not relied on to seal with an instrument in place, they nevertheless are expected to provide an effective closure with the instrument is removed.

In the past, zero closure valves have included flapper valves which permit the instrument to pass through the valve, but which are automatically biased to a closed position when the instrument is removed. One problem with the flapper valve is its complexity which generally equates to expensive and difficult manufacturing processes. An example of the flapper valve is disclosed by Moll et al. in U.S. Pat. No. 4,654,030.

Another type of zero closure valve is commonly referred to as a "duck bill" valve. This particular mechanism can form an effective zero closure, but it suffers from high friction forces which tend to inhibit insertion and removal of the instrument. The duck bill mechanism also tends to invert when the instrument is removed. An example of the "duck bill" valve is disclosed by Edwards, et al. in U.S. Pat. No. 4,566,493.

SUMMARY OF THE INVENTION

The present invention relates to access devices having zero closure valves which are moldable and therefore inexpensive to manufacture, which offer minimal resistance to instrument insertion and removal, which offer significant zero closure forces, and which automatically return to an operable configuration if inverted. The valve includes multiple walls which form fold segments that are automatically biased to a closed state and are responsive to the fluid pressure to maintain that state. At least three fold segments are desired in order to provide inner surfaces which intersect along lines that contact the instrument upon insertion. The reduced area provided by these lines of contact significantly reduce instrument insertion forces and enable the valve to easily unfold to an accommodating open state.

In accordance with one aspect of the invention, a surgical instrument having a longitudinal configuration and extending between a proximal end and a distal end, includes a housing having an inner surface defining a chamber and a cannula extending distally of the housing and having at least one lumen communicating with the chamber. A valve disposed in the housing has an outer wall with a conical configuration which forms a first seal with the inner surface of the housing, and a plurality of inner walls which form a second seal. The inner walls are foldable between a first position wherein the second seal closes the lumen of the cannula and a second position wherein the second seal opens the lumen of the cannula.

Another aspect of the invention includes a method for actuating a valve having an axis extending between a proximal end and an opposing distal end, the valve being actuated by an instrument having an elongate configuration. The method of actuation includes the steps of providing the valve with an outer wall defining a channel and a plurality of distal walls each having an outer surface and an inner surface. The distal walls extending distally inwardly of the outer wall to form a seal in the absence of the instrument. Inserting the instrument into the channel and contacting the inner surface of the distal walls with the instrument forces the distal walls outwardly as the instrument moves distally through the valve. Withdrawing the instrument from the valve inverts at least the distal walls to wipe the instrument during the withdrawing step.

These and other features and advantages of the invention will be more apparent with a discussion of preferred embodiments and reference to the associated drawings.

DESCRIPTION OF THE DRAWINGS

FIG. 1 is a side elevation view of a trocar partially cut away to illustrate a zero closure valve in one embodiment of the present invention;

FIG. 2 is a perspective view of the zero closure valve illustrated in FIG. 1;

FIG. 3 is an enlarged side elevation view of the zero closure valve of FIG. 2;

FIG. 4 is a front elevation view of the valve taken along lines 4—4 of FIG. 3;

FIG. 5 is a rear elevation view taken along lines 5—5 of FIG. 3;

FIG. 13 is a perspective view of a further embodiment of the invention wherein the a distal end of the valve has a convex configuration.

FIG. 18 is an axial cross section of the trocar showing a compound valve in a further embodiment of the invention.

DESCRIPTION OF PREFERRED EMBODIMENTS AND BEST MODE OF THE INVENTION

Figure 6:
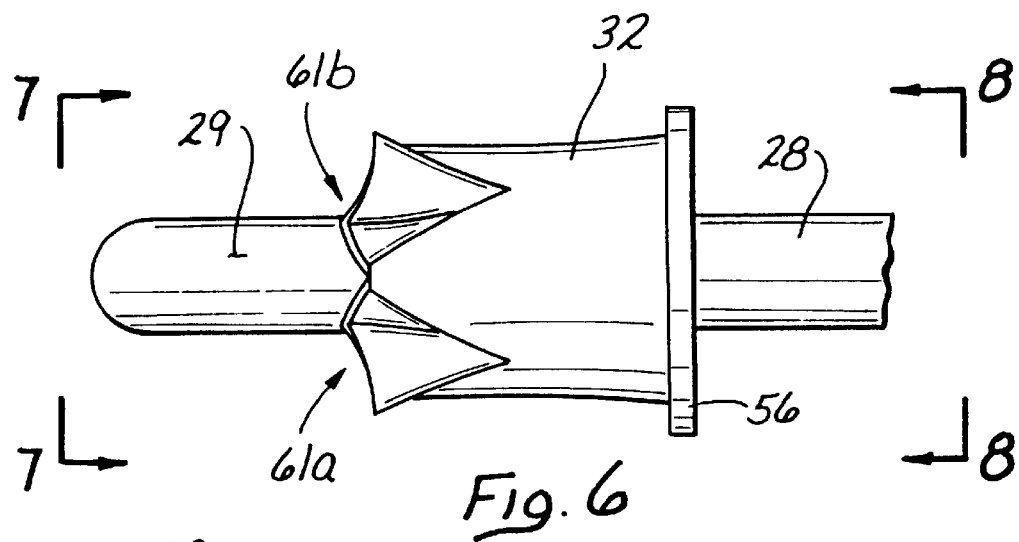
FIG. 6 is a side elevation view illustrating an instrument operatively positioned within the valve of FIG. 3.

A trocar is illustrated in FIG. 1 and designated generally by the reference numeral 10. The trocar 10 is represented of many types of surgical access devices which include a housing 12 and a cannula 14 which is adapted to extend across a body wall into a body cavity. In the case of the trocar 10, the cannula 14 is configured to extend through an abdominal wall 16 into a cavity, such as the abdominal cavity 18. The housing 12 includes a chamber 21 which is defined by an inner surface 23. This chamber 21 of the housing 12 communicates with a lumen 25 in the cannula 14 which is defined by an inner surface 27.

With these features, the trocar 10 is adapted to receive an instrument 28 having an elongate configuration and an outer surface 29. The instrument 28 is illustrated to be a pair of scissors having a length sufficient to pass through the trocar 10 and into the cavity 18 to perform a surgical operation. Although scissors are illustrated in FIG. 1, it will be understood that the instrument 28 may include any variety of devices such as needles, retractors, scalpels, clamps and various other surgical devices.

The housing 12 is configured to provide structural support for a seal mechanism, which in the preferred embodiment includes an aperture or septum seal 30 and a zero closure seal 32. It is the function of these seals 30, 32 to prevent the escape of any pressurized fluid from the cavity 18 whether the instrument 28 is operatively disposed in the trocar 10 or whether the instrument 28 is removed from the trocar 10. In either case it is desirable that the valves 30, 32 be configured to produce minimal friction forces as the instrument 28 is inserted into and removed from the trocar 10.

With these conflicting requirements for an effective, low-friction seal, the valve 30 is typically provided with an aperture 34 which has a circular cross section. This shape for the aperture 34 enables it to closely engage the outer surface 29 of the instrument 28 and to form a seal round the instrument 28 when it is operatively disposed.

The valve 30 will typically be formed of an elastomeric material so that the aperture 34 is biased to seal against the outer surface 29. In order to avoid significant friction forces, this aperture 34 is preferably sized to a diameter slightly less than the diameter of the surface 29. However, since various instruments and various diameters for the outer surface 29 may be required in a particular surgery, the valve 30 will typically have a configuration wherein the size of the aperture 34 is expandable in order to accommodate a range of instrument sizes.

Particularly for instruments having larger diameters, the aperture 34 will have some minimum diameter greater than zero in a normal state. As a consequence, the valve 30 is open when the instrument 28 is not positioned in the trocar 10. Although it has been contemplated to provide septum valves 30 with apertures 34 which are closed in a normal state, these valves generate significant friction forces for instruments 28 having typically larger diameters. As a consequence, septum valves, such as the valve 30, are usually not relied upon to provide full closure when the instrument 28 is removed.

This purpose is more typically served by a valve, such as the valve 32, which is commonly referred to as a zero closure valve. As noted, such valves of the past have included flapper valves, which are complex and expensive, and duck-bill valves which are characterized by high friction forces.

A preferred embodiment of the zero closure valve 32 is illustrated in FIGS. 2–5. In this embodiment, the valve 32 has an axis 41 which extends from a distal end 43 to a proximal end 45. A cylindrical outer wall 50 has an outer surface 52, and an inner surface 54 best shown in FIG. 5. The outer wall 50 typically extends from the distal end 43 toward the proximal end 45 where it engages an enlarged flange 56. This flange 56 extends radially outwardly of the wall 52 and is configured to form a seal with the housing 12 of the trocar 10.

Of particular interest to the present invention is the distal end of the valve 32 which is configured to provide reduced friction forces when the instrument 28 is inserted, as well as zero closure characteristics when the instrument 28 is removed. This distal end 43 includes three or more fold sections such as those designated by the reference numerals 61a, 61b, 61c, and 61d in FIG. 2.

In the illustrated embodiment, each of these sections has components which are similar to those in other sections. For simplicity, the reference numerals associated with these components will be the same, followed by a letter which designates the associated folding section. When the similar components are referred to collectively, the letters will be omitted.

The folding section 61 includes a pair of walls 63 and 65 which have a respective outer surfaces 67, 70 and inner surfaces 72, 74 (best shown in FIG. 5). In a preferred embodiment the walls 63 and 65 are parallel and have a thickness such as 0.06 to 0.10 inches which is equivalent to the thickness of the outer wall 50.

The outer surfaces 67, 70, and inner surfaces 72, 74 are planar in this embodiment and extend at angles which are dependent in part on the number of folding sections 61. In the embodiment of FIG. 2, the walls 63, 65 associated with each folding section 61 intersect each other at a first angle, designated 71 in FIG. 2, and intersect the axis 41 at the a second angle, designated 73 in FIG. 3.

The first angle 71 between the associated walls 63, 65 will typically be equal to 360° divided by the number of folding sections 61. In the illustrated embodiment, this first angle 71 between the walls 63 and 65 is 90°. In an embodiment including only three of the folding sections 61, the first angle 71 typically would be 120°. In an embodiment including five of the folding sections 61 the first angle 71 typically would be 72°.

In a symmetrical embodiment, the second angle 73 between each of walls 63, 65 and the axis 41, would be equal. This angle, which in the preferred embodiment is 26°, could be increased to accommodate a shorter axial length for the valve 32, or decreased to accommodate a longer axial length for the valve 32.

In the illustrated embodiment, the surfaces 67a, 70a provide the folding section 61a with a generally concave outer surface and intersect each other along a line 81a. This line of intersection 81a extends radially outwardly with progressive proximal positions until it contacts the surface 52 at a point 83a. As point 83 moves progressively toward the flange 56 the second angle 73 between each of the surfaces 67a, 70a and the axis 41 is reduced. The distance between the point 83 and the flange 56 should be sufficient to allow adequate flexure of the material without enabling a set or otherwise overstressing the material. In a preferred embodiment, the valve 30 has an overall length of 1.125 inches and the flange 56 has an axial thickness of 0.125 inches. The distance between the point 83 and the flange is 0.50 inches; it follows that the point 83 in this embodiment lies approximately half the distance between the distal end of the valve 30 and the flange 56.

The friction forces created when the instrument 28 is moved within the valve 32 are associated with the configuration of the inner surfaces 72 and 74. With reference to FIG. 5, it will be noted that these surfaces 72, 74 in the fold section 61 have a generally convex configuration and intersect each other along a line 85 which extends radially inwardly with progressive distal positions. The same relationship of the surfaces 72, 74 and lines 85 can exist for each of the fold sections 61. Thus for the fold section 61b, the surfaces 72b and 74b have a convex configuration and meet to define an inner line 85b which extends radially inwardly with progressive distal positions along the valve 32.

Since the innermost extension of the surfaces 72 and 74 is the respective line 85, it follows that an instrument 28 introduced along the axis 41 contacts the valve 10 only along these lines 85a–d. The instrument 28 preferably makes no contact with the surfaces 72a–d and 74a–d. This result is highly advantageous since the area of contact between the valve 32 and the instrument 28 is greatly reduced. It follows that friction forces associated with the insertion and removal of the instrument 28 are also greatly reduced.

Figure 7:
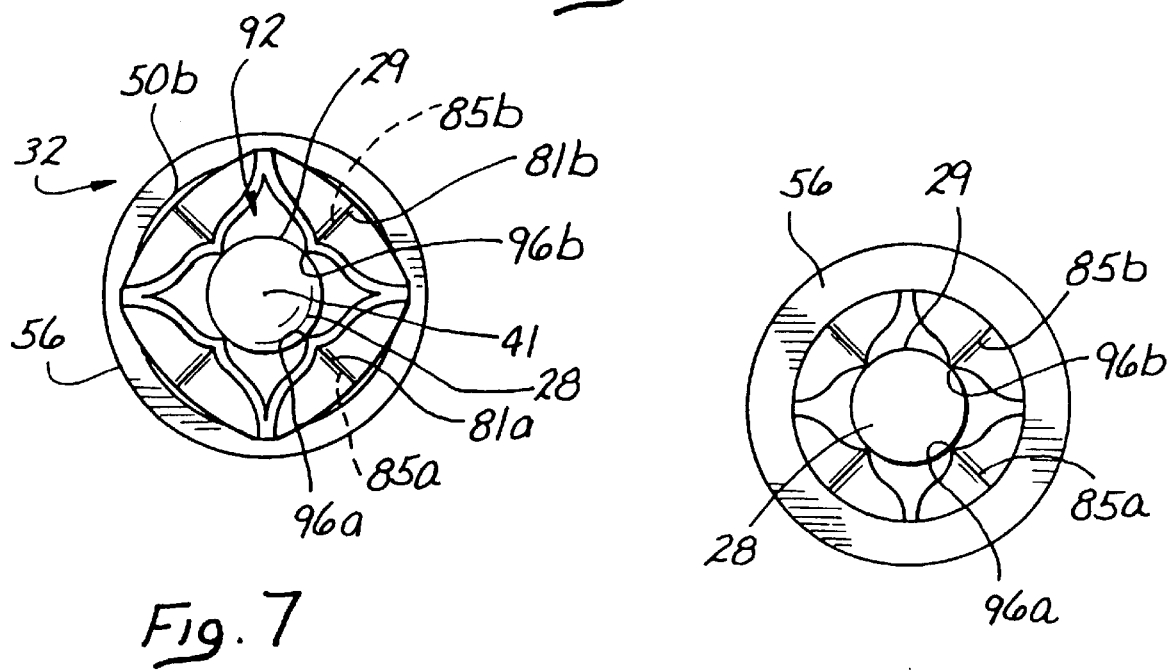
FIG. 7 is a front elevation view taken along lines 7—7 of FIG. 6.
Figure 8:
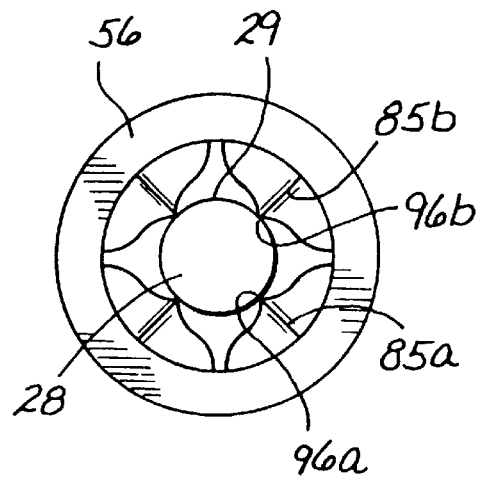
FIG. 8 is a rear elevation view taken along lines 8—8 of FIG. 6.

This feature relating to reduced friction is dramatically illustrated in FIGS. 6–8. As the instrument 28 is inserted into the valve 32 in its normally closed state, the fold sections 61 unfold to permit the instrument 28 to pass through the valve 32 in its open state. As the instrument 28 is inserted, its outer surface 29 contacts the valve 32 along the inner lines 85a–d forcing the fold section 61a–d radially outwardly to create and expand an opening 92 into the cannula 14. This opening 92 is best illustrated in the end views of FIG. 7 and FIG. 8. As the instrument 28 is introduced along the axis 41 it contacts the inner lines 85a–d along relatively short section designated 96a–d. Depending on the diameter of the instrument 28, this section 96a–d may be very short relative to the overall length of the line 85a–d, and in some cases, the section 96 of the line 85 may be substantially a point of contact. The narrower the line 85 and the shorter the section of contact 96, the lower the friction forces associated with insertion and removal of the instrument 28.

Although the seal 32 of the present invention is of particular interest for the low friction characteristics which it presents to the instrument 28, a primary purpose of the valve 32 is to provide a closure mechanism before the instrument 28 is inserted and after it is removed. In this case, the valve 32 provides a zero closure mechanism which is not possible with normal septum seals.

The zero closure state is best illustrated in FIG. 2 where it can be seen that the walls 63 and 65 which define the fold sections 61 extend distally to a surface 101 which is defined in a radial plane in this particular embodiment. As the instrument 28 is inserted into the valve 32, the valve moves from its normally closed state to an open state as illustrated in to FIGS. 6–8. The inner surfaces 72, 74 in adjacent fold sections 61 intersect along a slit 103 which extends from the inside of the seal 32 and through the distal surface 101. In a preferred embodiment each slit 103 extends from the inner surface 54 of the wall 50 to the axis 41. There is one slit for each of the fold sections 61. Thus in the illustrated embodiment including four of the fold section 61, there are four slits 103. If these four slits are equally spaced around the axis 41, alternate slits are co-planar and the slits 103 collectively define a cross.

Since a primary function of the valve 32 is to provide the zero closure mechanism it is important to consider the nature of the closure forces which exist in the absence of the instrument 28. The seal 32 is of particular advantage when it is disposed so that the surface 101 faces any fluid pressures such as those which may be associated with an insufflation gas, commonly used in laparoscopic surgery. Oriented in this direction, the outer surfaces 67, 70 associated with the walls 63 and 65, respectively, are oriented with at least a component facing distally of the valve 32. This presents the surfaces 67, 70 such that a fluid pressure on these surfaces will act to close the slits 103. In a particular embodiment wherein the surfaces 67, 70 are parallel to the slits 103, this component of force is directed perpendicular to the respective slit 103.

Figure 9:
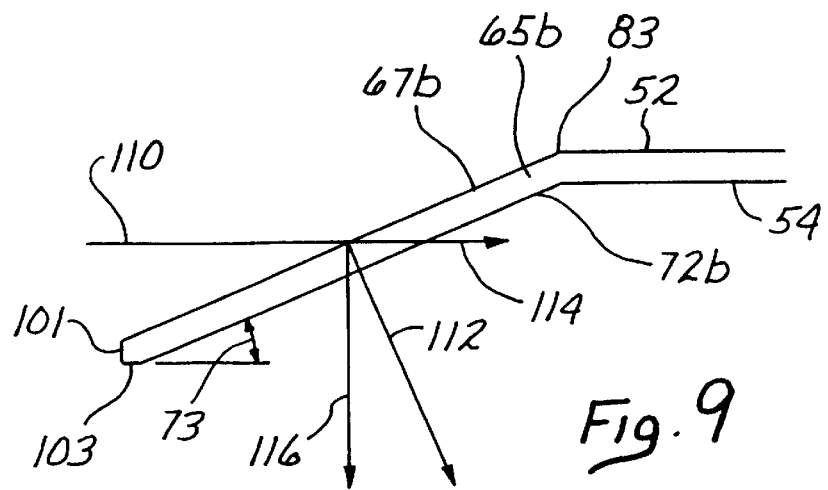
FIG. 9 is a diagram depicting closure forces typical for a valve of the present invention.

This can be better understood with reference to FIG. 9 wherein the wall 65b is shown in cross-section. In this diagram, an arrow 110 is representative of the axial direction from which fluid forces would emanate. As these forces impinge upon the outer surface 67b of the wall 65b, they create a force along arrow 112 which is perpendicular to the surface 67b. This arrow 112 can be separated into an axial component, represented by an arrow 114 and a radial component 116. It is the radial force represented by the arrow 116 which is perpendicular to the slit 103. Thus, response to the fluid pressure along the arrow 110 results in a component force along the arrow 116 which tends to move the slit 103 to a closed position.

It can now be seen that as the angle 73 between the surface 65b and the axis 41 increases, the length of the arrow 116 decreases providing a reduced closing force. This reduction in closing force must be compromised with the length of the valve 32 which can be reduced as the angle 73 increases. In the same manner, closing forces associated with the arrow 116 can be increased with a reduction in the angle 73 which will typically require a longer valve 32.

Figure 10:
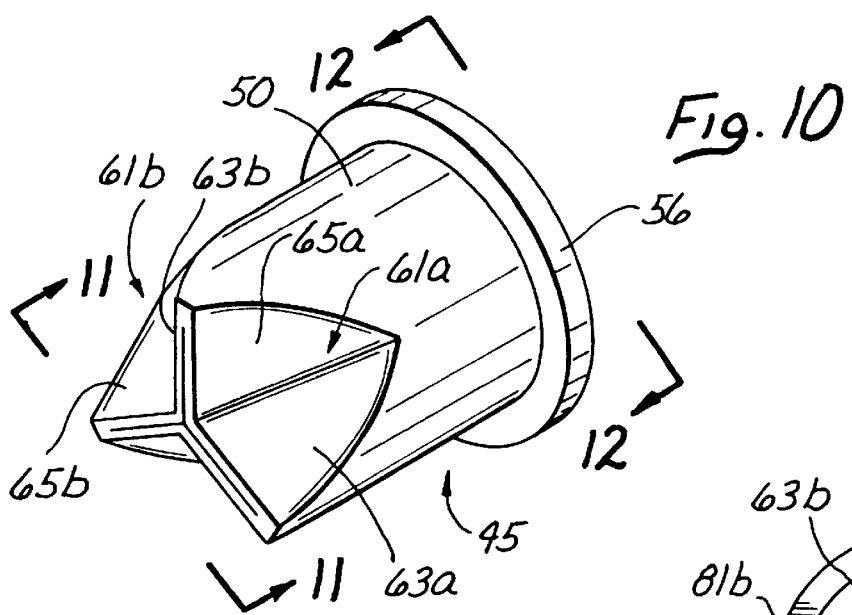
FIG. 10 is a perspective view similar to FIG. 2 of an embodiment including three fold sections.
Figure 11:
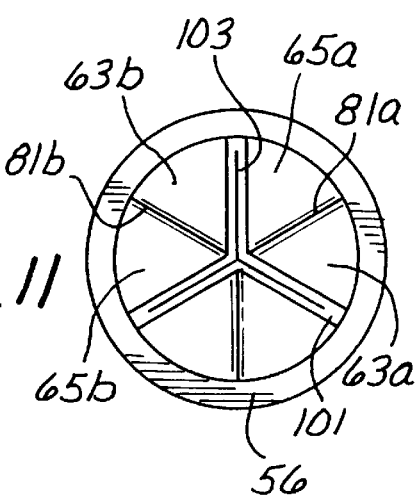
FIG. 11 is a front elevation view taken along lines 11—11 of FIG. 10.
Figure 12:
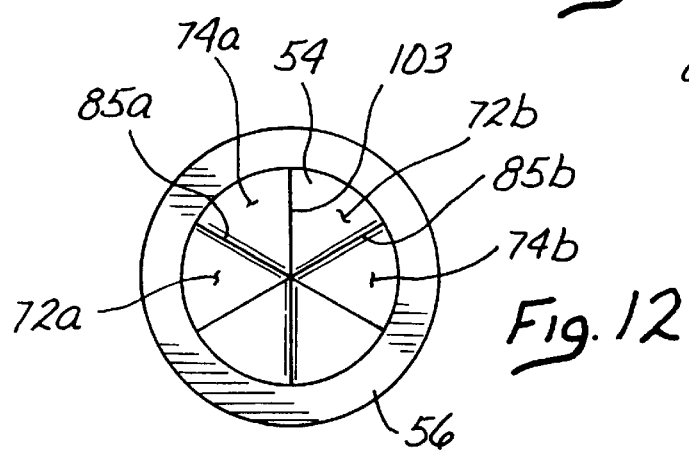
FIG. 12 is a rear elevation view taken along lines 12—12 of FIG. 10.

As previously mentioned, the concept of this invention is not to be limited by the number of folding sections 61. An embodiment of particular interest might include only three folding sections 61a–c as illustrated in FIGS. 10–12. In such an embodiment, the surfaces 67, 70 would be larger and for that reason could provide increased closing forces on the slits 103. Fewer folding sections 61 would also increase the circumferential distance separating the slits 103. This would equate to longer lever arms resisting the outward movement of the lines 81 as the valve 32 unfolds. Ultimately this could produce reduced friction forces opposing the entry of the instrument 28. With increased closing forces and decreased friction, this embodiment including three fold sections 61, could be of particular interest.

Also included in the invention is a preferred method for inserting the instrument 28 through the valve 32. In this method, the valve has the axis 41 and three or more of the fold sections 61. Each of these sections defines an opening such as the slit 103 and is movable between a first position wherein the slit 103 is in a closed state as illustrated in FIG. 2 and a second position wherein the slit 103 is in an open state as illustrated in FIG. 6. As the instrument 28 is introduced into the valve 32, it contacts the walls 63, 65 of the valve along the lines 85. With further insertion of the instrument, the fold sections 61 move from the closed first position to the open second position. When the instrument 28 is ultimately removed from the valve 32, the fold sections 61 return from the open second state illustrated in FIG. 6 to the closed first state illustrated in FIG. 2.

Orienting the valve 32 so that the outer surfaces 70, 72 face in the distal direction makes the valve 32 particularly valuable for use in a pressurized environment. For example, when the cannula 14 is introduced into the abdominal cavity for laparoscopic surgery, a commonly used insufflation gas will exert a pressure on the distally facing outer surfaces 67, 70. As previously disclosed with reference to FIG. 9, the forces generated by the insufflation gas will tend to force the valve 32 to its zero closure state.

A further embodiment of the invention is illustrated in the perspective view of FIG. 13. This embodiment is similar to that illustrated in FIGS. 2 and 10 except that the distal end 43 of the valve 30 is generally curved. This curve is preferably convex so that the surface 101 at the distal end of the valve 30 extends decreasingly, radially, outwardly with progressive distal positions along the axis 41. In a preferred embodiment, the surface 101, forms the quadrant of a circle. Thus the surface 101 is substantially perpendicular to the surface 52 at the axis 41 and substantially parallel to the axis 41 at the surface 52.

This particular embodiment having a curved distal end 43, has been found to offer improved characteristics for returning to its normal shape in the event of an inversion. While this feature is present to some extend in all of the foregoing embodiments, this particular embodiment appears to offer the greatest resistance to inversion and the greatest tendency for returning to its normal shape.

Figure 14:
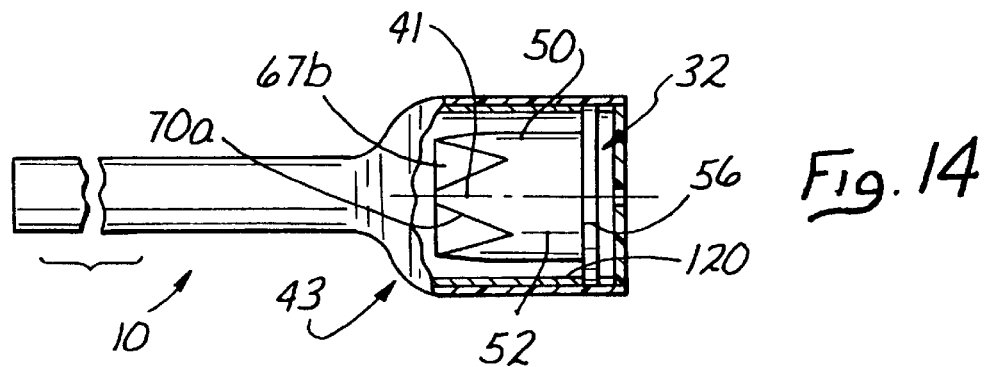
FIG. 14 is an axial cross section view of a further embodiment of the trocar and valve of the present invention.

A further embodiment of the invention is illustrated in FIG. 14 and includes a distal end 43 an outer wall 50 having an outer surface 52 and a proximal flange of 56. In this embodiment, the distal end 43 can be configured similar to any of the embodiments previously discussed. It is the outer wall 50 which differs from the foregoing embodiments in that it has a frusto-conical configuration rather than a cylindrical configuration. Thus the wall 50 forms a surface of rotation about axis 41 and extends radially inwardly with progressive distal positions along the axis 41.

This conical configuration of the outer wall 50 provides the valve 30 with significantly different characteristics which are of particular advantage when the instrument 28 is withdrawn. In the previous embodiments wherein the outer wall 50 has a generally cylindrical configuration, the valve 32 functions to prevent inversion when the instrument 28 is withdrawn. While a non-inverting embodiment may be of advantage is some situations, in other cases, the inversion may be equally desirable. It has been found, for example, that inversion of the valve 32 in response to withdrawal of the instrument 28 functions to wipe the instrument 28 as it is withdrawn from the trocar 10.

Figure 15:
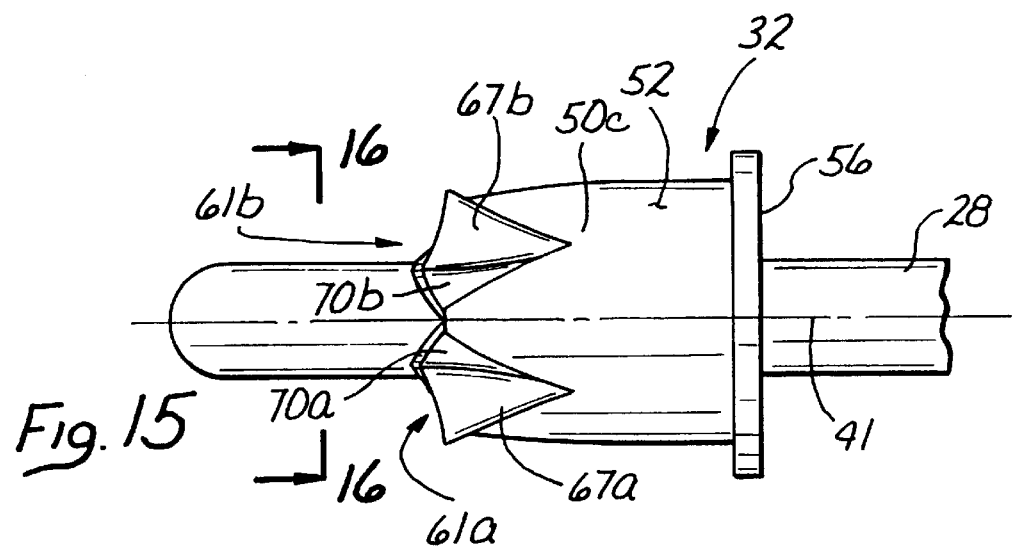
FIG. 15 is an axial cross section view of the valve illustrated in FIG. 14 with an instrument inserted into the valve.
Figure 16:
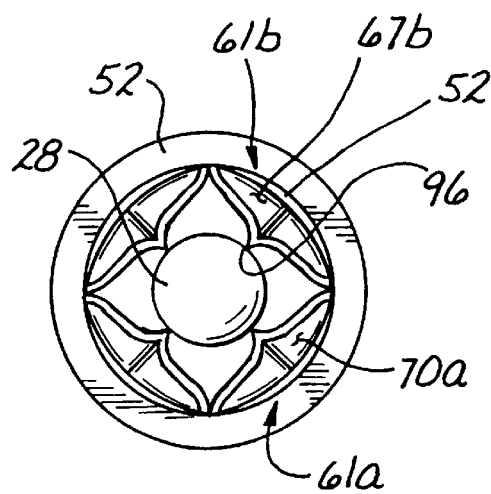
FIG. 16 is an end view and taken along lines 16—16 of FIG. 15.

This inversion of the outer wall 50 is facilitated in the embodiment of FIG. 14 by the conical configuration of the wall 50. This can be more easily understood with reference to FIG. 15 which is similar to FIG. 6. An end view of this FIG. 15 is shown in FIG. 16. These figures best illustrate the forces present on the valve 32 as the instrument 28 is removed from the valve 32, into the page in FIG. 16. As the instrument 28 is withdrawn the frictional contact between the short section 96 of the valve 32 and the instrument 28, tends to curl the fold sections 61 inwardly. In the embodiment of FIG. 7, this curling is resisted by the cylindrical outer wall 50 which remains at a fixed radial distance from the axis 41 of the valve 32. In contrast the conical outer wall 50 in the embodiment of FIG. 16 diverges from the axis 41 in the proximal direction, so that any resistance to inversion is greatly reduced. As the instrument 28 is withdrawn the fold section 61 is encouraged to curl radially inwardly. Thus, the conical configuration of the outer wall 50, which provides a circumference that increases with progressive proximal positions along the axis 41, actually facilitates inversion of the valve 32.

Figure 17:
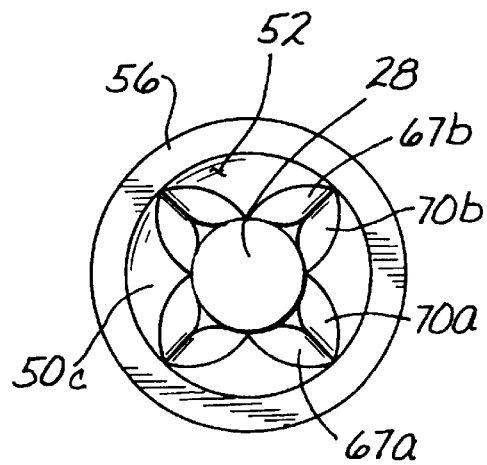
FIG. 17 is an end view similar to FIG. 16 and showing the instrument being withdrawn to promote inversion of the valve.

When the valve 32 inverts, the fold sections 61 turn outside in. The consequence of this inversion is to change contact with the instrument 28 from a line contact wherein the short sections 96 touch the instrument 28, to a surface contact wherein the outer surfaces of the fold sections 61, (for example the surfaces 67 and 70) touch the instrument 28. With this transition from line contact to surface contact, the entire outer surface of the instrument 28 can be wiped clean by the valve 32 as illustrated in FIG. 17.

In a further embodiment of the invention illustrated in FIG. 18, a valve 32 has a distal section 120 which can be similar to any of the embodiments previously discussed. This valve 32 also has an integral proximal section 122 in the form of a floating septum seal such as that disclosed and claimed in applicant's copending application Ser. No. __08/051,609 filed on Apr, 23, 1993 which is incorporated herein by reference. This combination valve 32 includes a circumferential ring 124 which is disposed between the distal section 120 and the proximal section 122. The trocar 10 of this embodiment includes the cannula 14 which is snap-fit to the housing 12 as shown by an arrow 126. A facial screw 128 is snap fit to the cannula 14 as shown by an arrow 130. A cap 132 is provided with a bayonet lock 134 which registers with tangs 136 carried by the housing 12.

The housing 12 is provided with an annular recess 138 to receive the ring 124 of the valve 32. With this ring sandwiched between the recess 138 of the housing 12 and a shoulder 141 on the cap 132, the outer surface of the valve 32 is effectively sealed around its perimeter to the housing 12d.

Although the invention has been disclosed with reference to specific embodiments and methods, it will be apparent to those skilled in the art that the concept can be structured in other embodiments, and the method can be carried out with other steps. For example, and without limitation, other embodiments might include more than four of the fold sections 61. Similarly, the outer surfaces 67, 70 defining the walls 64, 65 of the fold sections 61 could be angled in different directions. This angle of orientation may affect not only the closing forces but also the axial dimension of the valve 32 as previously discussed.

While the illustrated embodiments all terminate in a distal surface 101 which is disposed in a radial plane, it will be apparent that this distal surface can be disposed at other angles relative to the axis 41. Similarly, the symmetry illustrated and disclosed for the fold section 61, the surfaces 67 and 70, the length of the slits 103, and the length of the lines 81 and 85, could be varied to produce or asymmetrical embodiment.

The inner surfaces 54, 72 and 74 may also be varied in their respective shapes. Whenever possible, these various configurations should produce the point or line of contact, such as the line 85. As noted, this reduced area of contact will significantly reduce the friction forces associated with the insertion and removal of the instrument 28.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A valve having an axis extending between a proximal end and an opposing distal end, comprising:
   an outer wall forming a continuous surface around the axis, the continuous surface extending progressively radially inwardly between the proximal end to the distal end
   a flange extending radially outwardly at a proximal end of the outer wall;
   a plurality of fold sections extending inwardly of the outer wall and forming a continuous inner wall of the valve, each of the fold sections having an open state and a closed state;
   a first one of the fold sections having a generally concave distal facing surface and a generally convex proximal facing surface;
   a second one of the fold sections disposed in juxtaposition to the first fold section and defining with the first fold section a slit which is sealed when the fold sections are in the closed state and is unsealed when the fold sections are in the open state.

2. The valve recited in claim 1 wherein:
   each of the fold sections includes a first wall and a second wall; and
   the slit is formed by the first wall of the first fold section and the second wall of the second fold section.

3. The valve recited in claim 2 wherein the line of intersection extends radially inwardly with progressive distal positions along the axis of the valve.

4. The valve recited in claim 1 wherein the convex proximal facing surface includes:
   a first generally planar inner surface;
   a second generally planar inner surface; and
   the first surface intersects the second surface along a line.

5. The valve recited in claim 1 wherein the slit is defined in a plane which passes thorough the axis of the valve.

6. The valve recited in claim 5 wherein the plane of the slit is generally perpendicular to the axis of the valve.

7. The valve recited in claim 1 wherein the continuous surface is a surface of rotation around the axis of the valve.

8. The valve recited in claim 7 wherein the continuous surface has the configuration of the frustrum of a cone.

9. The valve recited in claim 8 wherein the cone has a base and the base of the cone is disposed in juxtaposition to the flange of the valve.

10. A valve adapted to receive an elongate instrument, and having an axis extending between a proximal end and a distal end, the valve comprising:
    an annular flange extending outwardly of the axis;
    an outer circumferential wall extending distally of the flange;
    a plurality of distal walls extending inwardly distally of the outer wall, the distal walls being adapted to form a seal when the instrument is absent from the valve and to engage the instrument when the instrument is received by the valve;
    the outer wall having a first circumference in proximity to the distal walls and a second circumference in proximity to the flange; and
    the second circumference being greater than the first circumference to facilitate inversion of the valve when the instrument is withdrawn from the valve wherein the outer wall extends progressively radially inward between the proximal end to the distal end.

11. The valve recited in claim 10 wherein the outer wall has the configuration of a cone.

12. The valve recited in claim 10 wherein:
    the distal walls each have an inner surface and an outer surface; and
    the outer surfaces of the distal walls are adapted to wipe the instrument when the valve inverts upon withdrawal of the instrument.

13. The valve recited in claim 12 wherein the inner surfaces of the distal walls intersect along a plurality of lines which contact the instrument when the instrument is inserted into the valve.

14. The method for actuating a valve having an axis extending between a proximal end and an opposing distal end, with an instrument having an elongate configuration, comprising the steps of:
    providing the valve with an outer wall defining a channel through the valve;
    providing the valve with a plurality of distal walls each having an outer surface and an inner surface, the distal walls extending distally inwardly of the outer wall to form a seal in the absence of the instrument;
    inserting the instrument into the channel;
    contacting the inner surface of the distal walls with the instrument;
    forcing the distal walls outwardly as the instrument moves distally through the valve;
    withdrawing the instrument from the valve; and
    inverting at least the distal walls of the valve outside in to wipe the instrument during the withdrawing step.

15. The method recited in claim 14 further comprising the step of providing the outer wall with the configuration of a cone.

16. The method recited in claim 15 wherein the third providing step includes the step of providing the outer wall with the configuration of a cone having a base and the method further comprises the step of orienting the outer wall with the base of the cone facing proximally of the valve.

17. The method recited in claim 14 wherein the third providing step includes the step of providing the outer wall with a circumference which decreases with progressive distal positions along the axis of the valve.

* * * * *